(12) United States Patent
Reich

(10) Patent No.: US 6,307,118 B1
(45) Date of Patent: Oct. 23, 2001

(54) DIGIT WOUND DRESSING

(76) Inventor: Marshall P. Reich, 1550 S. Potomac, Suite 350, Aurora, CO (US) 80012

( * ) Notice: Subject to any disclaimer, the term of this patent is extended or adjusted under 35 U.S.C. 154(b) by 0 days.

(21) Appl. No.: 08/862,818

(22) Filed: Mar. 17, 1997

(51) Int. Cl.⁷ .................................................. A61F 13/00
(52) U.S. Cl. .............................. 602/42; 602/44; 602/61; 602/79; 2/21
(58) Field of Search ........................... 602/22, 30, 41–43, 602/53, 60, 61.63, 79; 2/21, 163; D2/189

(56) References Cited

U.S. PATENT DOCUMENTS

| | | | |
|---|---|---|---|
| 549,748 | * | 11/1895 | Rate . |
| 1,471,948 | * | 10/1923 | Cox et al. . |
| 2,332,473 | * | 10/1943 | Salander .................................. 602/30 |
| 2,431,203 | * | 11/1947 | Sebastian . |
| 2,875,758 | * | 3/1959 | Fuazk et al. ........................ 602/41 X |
| 4,194,736 | * | 3/1980 | Loafman .................................. 2/21 X |
| 4,212,296 | * | 7/1980 | Schaar . |
| 4,654,896 | * | 4/1987 | Rinehart . |
| 5,086,763 | * | 2/1992 | Hathman ................................. 602/42 |
| 5,431,622 | * | 7/1995 | Pyrozyk et al. .................... 602/54 X |
| 5,662,599 | * | 9/1997 | Reich et al. ............................ 602/79 |
| 5,765,731 | * | 6/1998 | Callian .................................... 2/21 X |
| 5,843,018 | * | 12/1998 | Shesol et al. ........................... 602/79 |
| 5,897,519 | * | 4/1999 | Shesol et al. ........................... 602/79 |

* cited by examiner

*Primary Examiner*—Kim M. Lewis
(74) *Attorney, Agent, or Firm*—Edwin H. Crabtree; Ramon L. Pizzaro; Donald W. Margolis

(57) ABSTRACT

A digit wound dressing for use as a primary wound dressing or as a secondary wound dressing for digits on humans, animals and like applications. As a secondary digit wound dressing, the dressing can be used to hold a variety of different types of primary wound dressing such as sterile cotton gauze pads on top of a digit wound. The wound dressing includes an elongated bidirectional (stretches laterally along it's length) wrap which is adaptable for conforming to various sizes and shapes of digits. The wrap is made of a loose weave material and includes a releasable hook fastener at one end of the wrap. The hook fastener is used for releasable engagement with the loose weave material of the wrap when the wrap is secured around the digit. An outwardly extending ear is integrally formed on one side of the wrap. The ear is used to fold over and cover a tip of the digit. The ear also includes a releasable hook fastener so that when the ear is folded over and covers the tip of the digit, the ear is secured in place to a portion of the wrap. The folded ear is used to protect the tip of the digit and may also be used to hold a primary wound dressing in place.

20 Claims, 1 Drawing Sheet

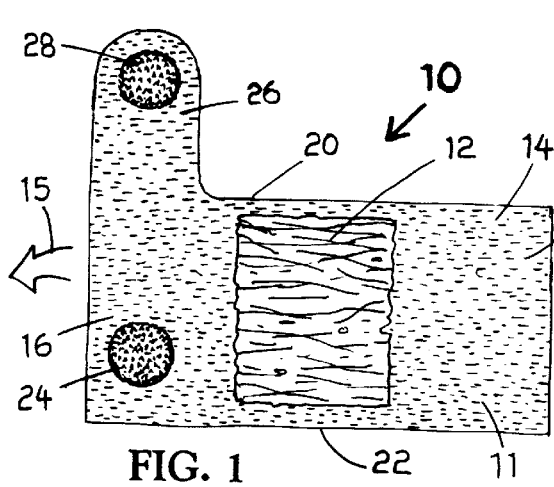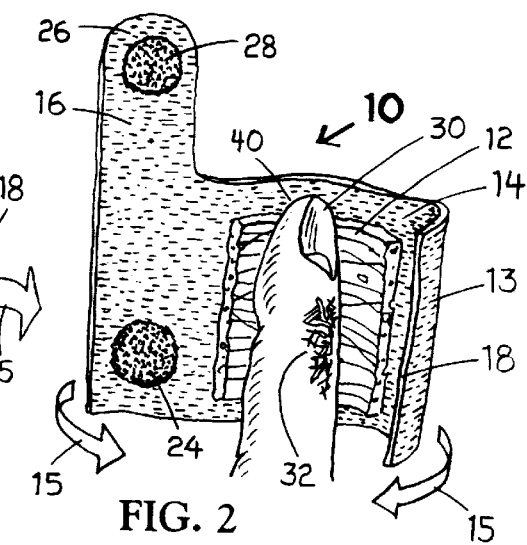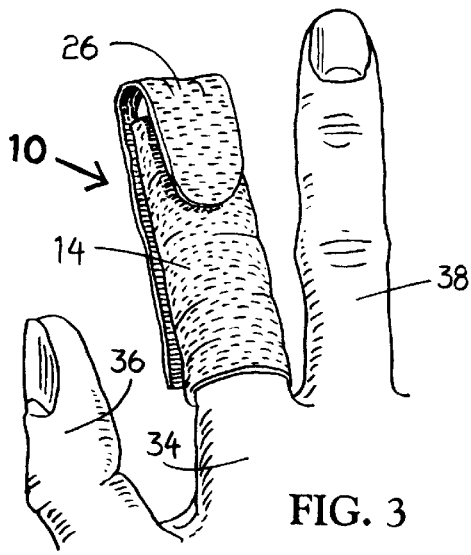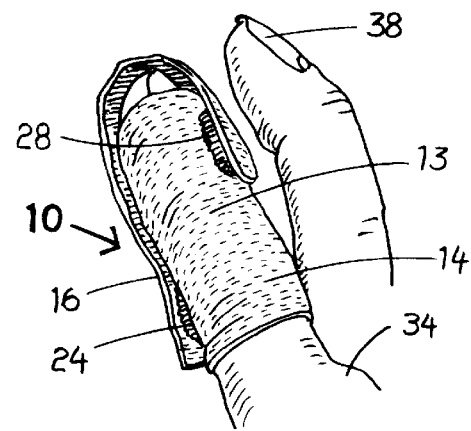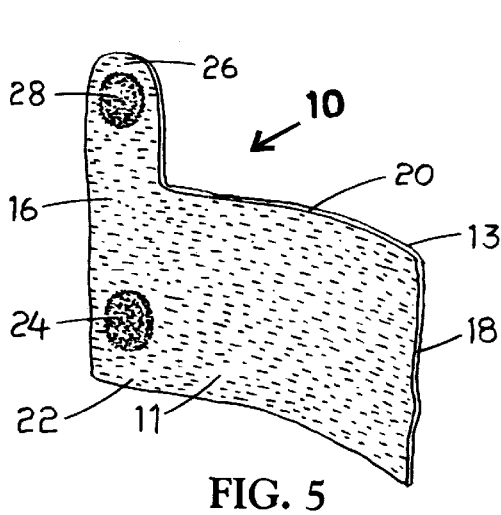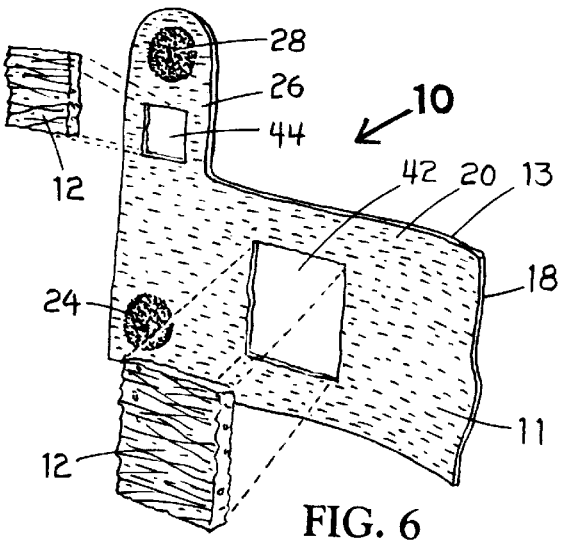

DIGIT WOUND DRESSING

BACKGROUND OF THE INVENTION (a) Field of the Invention

This invention relates to wound dressings and wound bandages and more particularly, but not by way of limitation, to a disposable, washable, reusable digit wound dressing that can be used both as a secondary wound dressing for holding various types of dressings on digits of humans, animals and similar applications.

(b) Discussion of Prior Art

Because of the complexity of wound healing, the function of a wound dressing may be integral to the success of that process. Wound dressings function as:

a. a protective barrier from outside sources of irritation.

b. provide for mechanical support to the fragile wound surface.

c. serve to form an occlusive barrier to provide an optimal environment for certain wound types.

d. function to absorb wound byproducts that tend to accumulate and complicate healing.

e. act as an agent for wound debridement which acts to clean and prepare a wound bed for healing.

f. may have value as an acceptable camouflage for unsightly wound appearances.

Digit wound dressing are quite often secured in place by the application of an adhesive to the skin. This seemingly simple and universal method of dressing fixation actually has limited applicability accompanied with a significant list of inadequacies, problems and patient dissatisfactions:

a. difficulty with conforming to some anatomic locations and contours, particularly in active body locations.

b. an increasing incidence of adhesive allergies resulting in blister formation, rashes, weeping wounds, scars, and permanent pigmentation problems.

c. inability to adhere in areas of raw, open wounds, or wounds with vulnerable scab formation.

d. lack of satisfactory adherence in hair bearing areas or areas of hypersensitivity.

e. pain associated with adhesive removal in hair bearing areas or areas of hypersensitivity.

f. adhesive system is not reusable when loosened by movement or moisture, thus necessitating reapplication.

g. lack of usefulness in wet to dry dressing situations. Due to the moist dressing, adhesives will not hold the dressings in place, making the wet to dry concept totally ineffective.

h. possibly the most important of issues is that a wound dressing, if not properly chosen, can significantly retard and limit wound healing.

i. adhesives used will stick to protective gloves now used by all handlers of wound products, often tearing the gloves and making them ineffective as a protective barrier.

Also, traditional digit wound dressings are applied with various tapes, elastic wraps, gauze wraps, roller gauze and tube gauze. These dressing wraps have intrinsic negative aspects as compared to the subject digit wound dressing described by virtue of:

a. restricted areas of usefulness in terms of adhesives. Adhesives also cannot easily be "readjusted".

b. wraps produce significant bulk of material and that bulk also reduces the gas exchanged from the wound surface.

c. wraps obscure the nature and quantity of wound drainage.

d. wraps such as tube gauze using a cage applicator require a second person to apply. This may lead to other individuals having to assist and/or provide additional care for the patient. The applying and removing the tube gauze from a digit can be extremely painful.

e. wraps often require a secondary means of fixation which thereby complicates the dressing change process.

f. wraps lead to waste of materials or increased production of biohazardous materials.

g. prior art elastic wraps may cause decreased blood flow to the digits.

Heretofore there have been a variety of different types of wound dressings using adhesives and stretchable wraps such as described in the following patents.

U.S. Pat. No. 4,732,146 to Fasline et al. discloses a surgical wound dressing device having a frame with an opening for receiving different types of wound dressings. A dressing is held in place by straps attached to one side of the frame with one end of the straps including releasable Velcro fasteners.

U.S. Pat. No. 4,917,112 to Kalt describes a bandage having an opening with the opening covered with a transparent membrane. The membrane is designed to allow air and vapors to permeate outward from the wound and prevent contaminants from entering in the opposite direction.

In U.S. Pat. No. 4,909,243 to Frank et al., a two piece wound dressing is shown having an adhesive layer on one side of a baseplate with an opening in the baseplate to expose the wound and the epithelium area around the wound. A second adhesive layer on one side of a wound pad secures a wound dressing above the opening in the baseplate.

U.S. Pat. No. 4,907,579 to Kum, U.S. Pat. No. 5,167,613 to Karami et al., and U.S. Pat. No. 3,779,242 to McCullough disclosed different types of adhesive bandages for providing open areas to wounds to enhance healing. In U.S. Pat. No. 5,036,838 to Sherman, a foam plastic orthopedic fabric is described having a Velcro tab at one end of the fabric.

In U.S. Pat. No. 4,470,410 to Elliott a stretchable sleeve is shown with Velcro fasteners at the ends of the sleeve. The sleeve includes a central opening with a releasable flap for retaining an intravenous tube or the like.

U.S. Pat. No. 4,709,695 to Kohn et al., U.S. Pat. No. 4,399,816 to Spangler, U.S. Pat. No. 5,086,763 to Hathman, and U.S. Pat. No. 4,926,883 to Strock all describe different types of wound surrounding dressings and bandages. Also U.S. Pat. No. 4,190,054 to Brennan and U.S. Pat. No. 4,658,811 to Beaird disclose stretchable bandages having loop and hook type attachment ends for encircling the head of a patient.

In U.S. Pat. No. 5,456,660 to the subject inventor and Dr. Barry F. Shesol, a wound dressing support device is described for holding a variety of standard gauze pads in place on top of an open wound. The device includes an elongated bidirectional wrap with a window opening therethrough. Around the sides of the window is a non-adhesive fastener for releasably engaging a portion of the sides of the gauze pad.

None of these prior art patents disclose the unique structure and advantages of the subject invention as described herein when addressing the need of a disposable wound wrap for digits.

SUMMARY OF THE INVENTION

In view of the foregoing, it is an object of the present invention to provide a digit wound dressing holder which acts as a secondary wound dressing and is easy to apply and holds different types of primary wound dressing such as a sterile gauze pad in place on top of a wound. Also in certain application, the digit wound dressing can be used as a primary wound dressing without using a sterile gauze pad or similar dressing. Further, the digit wound dressing can be used as a splint holder when a digit is broken. Still further, the wound dressing can be used as a wrap around a male penis after circumcision and for other penile injuries. The digit wound dressing uses a bidirectional wrap material which prevents slippage from the digit and provides for infinite adjustments when securing the wound wrap around the digit.

Another object of the invention is to provide a digit wound dressing that eliminates the need of using a standard tube gauze system which causes pain when applying the system and during it's removal. Using the subject invention, the patient can easily change the digit wound wrap and primary wound dressing with ease and without the need of assistance.

Yet another object of the invention is the dressing is provided with hook fasteners at one end of a wrap for engaging a portion of loop like material of the wrap allowing for easy adjustment in either loosing or tightening the wrap when a gauze pad is received over the wound. The unit is designed so that there is no excess material or use of supplies, thus keeping down the amount of bihazardous waste material to be disposed.

A further object of the dressing is that it's lightweight, nonconstricting, reusable, washable, non-adhesive, disposable, versatile and able to be applied by a single individual. The dressing allows for frequent dressing changes with minimal disruption to the wound bed or local tissues. Also, the dressing can be used to stop minor hemorrhages.

Still another object of the dressing is its adaptability to different digits on a human body, on animals and similar applications. The digit dressing preserves the integrity of the skin by avoiding adhesives and abrasive materials.

The wound dressing includes an elongated bidirectional wrap which is adaptable for conforming to various sizes and shapes of digits. The wrap is made of a loose weave material and includes a releasable hook fastener at one end of the wrap. The hook fastener is used for releasable engagement with the loose weave material of the wrap when the wrap is secured around the digit. An outwardly extending ear is integrally formed in one side of the wrap. The ear is used to fold over and cover a tip of the digit. The ear also includes a releasable hook fastener so that when the ear is folded over and covers the tip of the digit, the ear is secured in place to a portion of the wrap. The folded ear is used to protect the tip of the digit and may also be used to hold a primary wound dressing in place.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a front view of the digit wound dressing in an open position with a primary wound dressing such as a sterile cotton gauze pad mounted thereon.

FIG. 2 is a perspective view of the digit wound dressing positioned for receipt around an index finder having an open wound.

FIG. 3 is a front view of the digit wound dressing received around and secured to an index finger of a human hand.

FIG. 4 is a side view of the dressing on the index finger as shown in FIG. 3.

FIG. 5 is a perspective view of a digit wound dressing without a primary wound dressing secured thereto.

FIG. 6 is a perspective view of a digit wound dressing with a window through an elongated wrap of the dressing and a gauze pad positioned for receipt over the window.

DESCRIPTION OF THE PREFERRED EMBODIMENTS

In FIG. 1, the digit wound dressing for use as a secondary wound dressing for digits on humans, animals and like applications is shown having a general reference numeral 10. As a secondary digit wound dressing, the dressing 10 can be used to hold a variety of different types of primary wound dressing such as a sterile cotton gauze pad 12 on top of an inside 11 of an elongated wrap 14. The wrap also includes an outside 13. The wrap 14 is bidirectional and stretches laterally along the wrap's length indicated by arrows 15. The wrap 14 includes a first end 16, a second end 18, a first side 20 and a second side 22. The wrap 14 is adaptable for conforming to various sizes and shapes of digits. The wrap 14 is made of a loose weave material and includes a first releasable hook fastener 24 at the first end 16 of the wrap 14. The hook fastener 24 is used for releasable engagement with the loose weave material along the length of the wrap 14 when the wrap is secured around the digit. The dressing 10 also includes an outwardly extending ear 26 integrally formed in the first side 20 of the wrap 14. The ear 26 is used to fold over and cover a tip of the digit. The ear 26 also includes a second releasable hook fastener 28 so that when the ear 26 is folded over and covers the tip of the digit, the ear is secured in place to a portion of the wrap 14.

In FIG. 2, a perspective view of the digit wound dressing 10 is shown positioned for receipt around an index finder 30 having an open wound 32. In this view, the gauze pad 12 is shown ready for receipt on top of the open wound 32. The second end 18 is then wrapped around the index finger 30 and the first hook fastener 24 is then secured on top of a portion of the second end 18 of the wrap 14. By using the hook fastener 24 and the loose weave material of the wrap 14, infinite adjustments can be made along the length of the wrap 14 for loosening and tightening the digit wound dressing 10 on the index finger 30.

In FIG. 3, a front view of the digit wound dressing 10 is shown received around and secured to the index finger 30 of a human hand 34 having a thumb 36 and middle finger 38. Note in this drawing, the ear 26 has been folded over a tip 40 of the index finger 30 for protecting this portion of the finger 30. While not shown in the drawings, it can be appreciated that the ear 26 can be used to hold the gauze pad 12 in place should there be an injury at the tip 40 of the finger 30.

In FIG. 4, a side view of the dressing 10 on the index finger 30 as shown in FIG. 3. In this view, the first hook fastener 24 can be seen releasably secured to the wrap 14 and the second hook fastener 24 folded over and releasably secured to a portion of the wrap 14.

In FIG. 5, a perspective view of a digit wound dressing 10 is shown without a primary wound dressing secured thereto. While the gauze pad 12 is shown, it can be appreciated that a variety of different types of primary dressings can be used in conjunction with the subject invention. In this drawing, the digit wound dressing 10 is used as a primary dressing for receipt around a digit. By the nature of the construction of the wrap 14, the dressing 10 can easily conform to different sizes and shapes of digits and secured thereto.

In FIG. 6, a perspective view of another embodiment of the digit wound dressing 10 is shown with a first window 42 through the elongated wrap 14 and disposed along a length of the wrap 14. The first window 42 allows for visual inspection from the outside 13 of the wrap 14 looking in. Using the first window 42, the gauze pad 12 can be observed relative to the nature of the wound drainage, the amount of drainage, and when the dressing needs to be changed.

Also, a second window 44 if desired may be placed in the ear 26 for observing a gauze pad 12 placed over a wound on the tip 40 of the digit 30. Further, it can be appreciated that other sizes and shapes of windows may be placed at other locations along the length of the wrap 14.

While the invention has been particularly shown, described and illustrated in detail with reference to the preferred embodiments and modifications thereof, it should be understood by those skilled in the art that changes in form and detail may be made therein without departing from spirit and scope of the invention as claimed, except as precluded by the prior art.

The embodiments of the invention for which an exclusive privilege and property right is claimed are defined as follows:

1. A digit wound dressing anatomically adapted for receipt around a human and animal digit and over a tip or distal end of the digit, the digit wound dressing comprising:
    an elongated bidirectional wrap made of loose weave material, said wrap stretched along a length thereof, said wrap having a first end, a second end, a first side and a second side, said wrap dimensioned specifically for circumferential receipt around the sides, the front and the back of the digit and along the length of the digit, the first side of the wrap disposed next to the distal end of the digit;
    a first securing means disposed on the first and of said wrap, said first securing means for releasable engagement of a portion of the loose weave material in the second end of said wrap and holding said wrap on the digit;
    an ear, said ear integrally formed along a length of the first side of said wrap and extending outwardly and at a right angle from the length of the first side, said ear dimensioned specifically for covering the distal end of the digit; and
    a second securing means disposed on said ear, said second securing leans for releasable engagement of a portion of the loose weave material of said wrap when said ear is folded over the distal end of the digit;
    whereby said bidirectional wrap allowing for infinite adjustment when said first securing means is engaged with the second end of said wrap for control of various degrees of tightness on the digit.

2. The digit wound dressing as described in claim 1 wherein said first securing means is a first hook fastener, said first hook fastener adapted for releasably engaging the loose weave material of said wrap.

3. The digit wound dressing as described in claim 1 wherein said second securing means is a second hook fastener, said second hook fastener adapted for releasably engaging the loose weave material of said wrap.

4. The digit-wound dressing as described in claim 1 further including a primary wound dressing received on a portion of said wrap.

5. The digit wound dressing as described in claim 4 wherein said primary wound dressing is a sterile cotton gauze pad.

6. The digit wound dressing as described in claim 1 further including a primary wound dressing received on a portion of said ear.

7. The digit wound dressing as described in claim 6 wherein said primary wound dressing is a sterile cotton gauze pad.

8. A digit wound dressing anatomically adapted for receipt around a human and animal digit and over a tip or distal end of the digit, the digit wound dressing comprising:
    an elongated bidirectional wrap made of loose weave material, said wrap stretched along a length thereof, said wrap having a first end, a second end, a first side and a second side, said wrap dimensioned specifically for circumferential receipt around the sides, the front and the back of the digit and along the length of the digit, the first side of the wrap disposed next to the distal end of the digit;
    a first securing means disposed on the first end of said wrap, said first securing means for releasable engagement of a portion of the loose weave material in the second end of said wrap and holding said wrap on the digit;
    a first primary wound dressing received on a portion of said wrap;
    an ear, said ear integrally formed along a length of the first side of said wrap and extending outwardly and at a right angle from the length of the first side, said ear dimensioned specifically for covering the distal end of the digit; and
    a second securing means disposed on said ear, said second securing means for releasable engagement of a portion of the loose weave material of said wrap when said ear is folded over the distal end of the digit;
    whereby said bidirectional wrap allowing for infinite adjustment when said first securing means is engaged with the second end of said wrap for control of various degrees of tightness on the digit.

9. The digit wound dressing as described in claim 8 wherein said first securing means is a first hook fastener, said first hook fastener adapted for releasably engaging the loose weave material of said wrap.

10. The digit wound dressing as described in claim 8 wherein said second securing means is a second hook fastener, said second hook fastener adapted for releasably engaging the loose weave material of said wrap.

11. The digit wound dressing as described in claim 8 wherein said first primary wound dressing is a sterile cotton gauze pad.

12. The digit wound dressing as described in claim 8 further including a second primary wound dressing received on a portion of said ear.

13. The digit wound dressing as described in claim 12 wherein said second primary wound dressing is a sterile cotton gauze pad.

14. A digit wound dressing anatomically adapted for receipt around a human and animal digit and over a tip or distal end of the digit, the digit wound dressing comprising:
    an elongated bidirectional wrap made of loose weave material, said wrap stretched along a length thereof, said wrap having a first end, a second end, a first side and a second side, said wrap dimensioned specifically for circumferential receipt around the sides, the front and the back of the digit and along the length of the digit, the first side of the wrap disposed next to the distal end of the digit;
    a first primary wound dressing received on a portion of said wrap, said first primary wound dressing adapted for receipt over a wound on the digit when said wrap is received around and secured to the digit;

a first window in said wrap, said first primary wound dressing framed against sides of said first window in said wrap;

a first securing moans disposed on the first end of said wrap, said first securing means for releasable engagement of a portion of the loose weave material in the second end of said wrap and holding said wrap on the digit;

an ear, said ear integrally formed along a length of the first side of said wrap and extending outwardly and at a right angle from the length of the first side, said ear dimensioned specifically for covering the distal end of the digit; and a second securing means disposed on said ear, said second securing means for releasable engagement of a portion of the loose weave material of said wrap when said ear is folded over the distal end of the digit;

whereby said bidirectional wrap allowing for infinite adjustment when said first securing means is engaged with the second end of said wrap for control of various degrees of tightness on the digit.

15. The digit wound dressing as described in claim 14 wherein said first securing means is a first hook fastener, said first hook fastener adapted for releasably engaging said wrap.

16. The digit wound dressing as described in claim 14 wherein said second securing means is a second hook fastener, said second hook fastener adapted for releasably engaging said wrap.

17. The digit wound dressing as described in claim 14 wherein said first primary wound dressing is a sterile cotton gauze pad.

18. The digit wound dressing as described in claim 14 further including a second primary wound dressing received on a portion of said ear.

19. The digit wound dressing as described in claim 18 wherein said second primary wound dressing is a sterile cotton gauze pad.

20. The digit wound dressing as described in claim 18 further including a second window in said ear, said second primary wound dressing framed against sides of said second window in said ear.

\* \* \* \* \*